(12) United States Patent
Gokaraju et al.

(10) Patent No.: US 8,568,802 B2
(45) Date of Patent: Oct. 29, 2013

(54) **PROCESS FOR PRODUCING ENRICHED FRACTIONS OF TETRAHYDROXYCURCUMIN AND TETRAHYDROTETRAHYDROXY-CURCUMIN FROM THE EXTRACTS OF *CURCUMA LONGA***

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Venkateswarlu Somepalli, Andhra Pradesh (IN)

(73) Assignee: Laila Impex, Vijayawada, IN (US)

( * ) Notice: Subject to any disclaimer, the term of this patent is extended or adjusted under 35 U.S.C. 154(b) by 929 days.

(21) Appl. No.: 12/083,105

(22) PCT Filed: Oct. 13, 2005

(86) PCT No.: PCT/IN2005/000337
§ 371 (c)(1),
(2), (4) Date: Mar. 10, 2010

(87) PCT Pub. No.: WO2007/043058
PCT Pub. Date: Apr. 19, 2007

(65) Prior Publication Data
US 2010/0168248 A1    Jul. 1, 2010

(51) Int. Cl.
*A61K 36/9066* (2006.01)
*A61K 36/00* (2006.01)

(52) U.S. Cl.
USPC .......................................... 424/756; 424/725

(58) Field of Classification Search
USPC .................................. 424/756, 725
See application file for complete search history.

(56) References Cited

U.S. PATENT DOCUMENTS

| | | | |
|---|---|---|---|
| 5,266,344 A * | 11/1993 | Mimura et al. | 426/546 |
| 6,900,356 B2 * | 5/2005 | Gokaraju et al. | 568/313 |
| 2002/0197216 A1 * | 12/2002 | Majeed et al. | 424/59 |
| 2006/0165812 A1 * | 7/2006 | Charron | 424/600 |

FOREIGN PATENT DOCUMENTS

| | | |
|---|---|---|
| EP | 1 108 419 A1 * | 6/2001 |
| WO | WO-9703674 | 12/1997 |

OTHER PUBLICATIONS

Chen et al. Curcumin and its Analogues as Potent Inhibitors of Low Density Lipoprotein Oxidation: H-Atom Abstraction From the Phenolic Groups and Possible Involvement of the 4-Hydroxy-3-Methoxyphenyl Groups; Free Radical Biology & Medicine 40 (2006) 526-535.*
Mazumder et al. Curcumin Analogs With Altered Potencies Against HIV-1 Integrase as Probes for Biochemical Mechanisms of Drug Action; J. Med. Chem, 1997, 40, pp. 3057-3063.*
Roughley et al. Experiments in the Biosynthesis of Curcumin; J. Chem. Soc., Prekins Trans. 1 (1973), pp. 2379-2388.*
STN Registry Database: CN 1,6-Heptadiene-3,5-dione, 1-(3,4-dihydroxyphenyl)-7-(4-hydroxy-3-methoxyphenyl); Apr. 30, 2007, one page.*
STN Registry Database: 3,5-Heptanedione, 1-(3,4-dihydroxyphenyl)-7-(4-hydroxyphenyl); 2002/0197216; May 2, 2007, one page.*
Toshihiko et al. Antioxidative Activity of Tetrahydrocurcumin; T. International Congress Series; Oxygen Radicals; (1992) pp. 801-804.*
Toshihiko et al. Antioxidative Activity of Tetrahydrocurcumin; Biosci. Biotech. Biochem., 59 (9), pp. 1609-1612 (1995).*
Venkateswarlu et al. Synthesis and Biological Evaluation of Polyhydroxycurcuminoids; Bioorganic & Medicinal Chemistry 13 (2005) pp. 6374-6380.*

* cited by examiner

*Primary Examiner* — Patricia Leith
(74) *Attorney, Agent, or Firm* — Kramer Amado, P.C.

(57) ABSTRACT

A process for producing an enriched fraction of tetrahydoxycurcumin containing, tetrahydroxycurcumin, demethylcurcumin, demethylmonodemethoxycurcumin and bis-d.emethoxycurcumin and colorless tetrahydroderivatives thereof. The process consists of demethylation of natural curcumins, obtained, in turn, from the organic solvent extract of turmeric from *Curcuma* species. The said enriched fraction of tetrahydroxycurcumin is subjected to hydrogenation to get colorless tetrahydrotetrahydroxycurcumin enriched fraction. The enriched fractions of tetrahydroxycurcumin and colorless tetrahydrotetrahydroxycurcumin exhibits potent antioxidative action and reduces inflammation.

8 Claims, No Drawings

PROCESS FOR PRODUCING ENRICHED FRACTIONS OF TETRAHYDROXYCURCUMIN AND TETRAHYDROTETRAHYDROXY-CURCUMIN FROM THE EXTRACTS OF *CURCUMA LONGA*

The invention relates to a process for producing enriched fractions of tetrahydroxycurcumin and its tetrahydroderivative, tetrahydrotetrahydroxycurcumin. These enriched fractions exhibit potent antioxidative action and reduce inflammation. The products of the present invention are suitable as food additives, nutraceutical or cosmoceutical applications.

TECHNICAL FIELD

Free radicals play a major role in the initiation and progression of a wide range of pathological diseases like cancer, Alzheimer's, Parkinson's, and cardiovascular diseases. In the food industry, free radicals have been found to be responsible in the deterioration of foods during processing and storage In view of this, considerable attention has been given to the addition of antioxidants in foods and supplementation of antioxidants to biological systems to scavenge free radicals. The antioxidative compounds can be classified into two types: phenolics and β-diketones. Phenolic compounds exert their antioxidant activity by acting primarily as hydrogen atom donators, therby inhibiting the propagation of radical chain reactions. Antioxidant potential of the phenolics depends on the number and arrangement of phenolic hydroxyl groups, as well as the nature of the other substituents on the aromatic rings. Few natural products, like curcuminoids have both phenolic and β-diketone groups in the same molecule and thus became strong antioxidants. Curcumins, the phenolic diarylheptanoids, are characteristic yellow coloured constituents of turmeric (*Curcuma longa*) and are widely used in neutaceuticals, foods and cosmetics. FIG. 1, shows the chemical structures of curcumins: curcumin, monodemethoxycurcumin, bisdemethoxycurcumin, tetrahydroxycurcumin and herein after referred as C, MDC, BDC, TC. These compounds were reported to poseses antioxidant, anti-inflammatory, anticancer, Alzheimer's and antiviral properties. Of all the four curcumins, TC shows most potent anticancer, antioxidative and inflammatory activity. But the natural curcumin mixture contains TC in very low concentration (0-5%) depending on the raw material.

Presently, there has been a tremendous surge in demand for non-steroidal, plant based anti-inflammatory agents. 5-Lipoxygenase is the key enzyme for the biosynthesis of leukotrienes and 5(S)-HETE, the important mediators for inflammatory, allergic and obstructive process, from arachidonic acid. 5-Lipoxygenase is the target enzyme for identifying inhibitors, which have potential to cope with a variety of inflammations and hypersensitivity-based human diseases including asthma, arthritis, bowl diseases such as ulcerative colitis and circulatory disorders such as shock and ischaemia.

Because of proven safe, non-toxic nature of curcuminoids and the lack of enriched tetrahydroxycurcumin fraction to address the above problems, it is therefore an object of the present invention to provide enriched tetrahydroxycurcumin as a safe dietary supplement, which treats inflammatory diseases, free radical mediated diseases and nutraceutical and cosmetic applications.

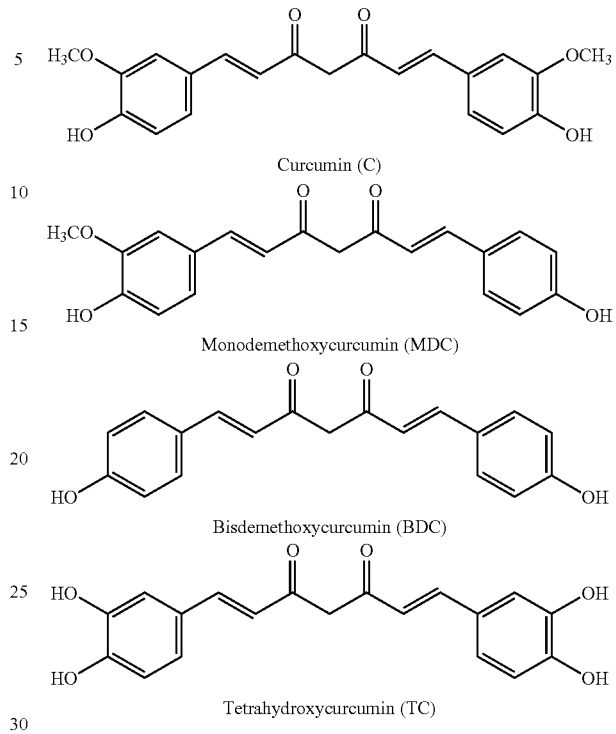

FIG.-1: Chemical structures of the curcumins of Curcuma longa.

DISCLOSURE OF THE INVENTION

The present invention relates to a process for manufacturing an enriched fraction of tetrahydroxycurcumin from the extract of turmeric (*Curcuma* species), which contains tetrahydroxycurcumin (TC), along with demethylcurcumin (DC), demethyldemethoxy-curcumin (DMDC) and bisdemethoxycurcumin (BDC) as minor compounds. The present invention also encompasses the above said fraction for administration to animals including mammals, and a method of treating various inflammatory conditions and also a method of preventing various oxidative disease conditions by administering the inventive fraction.

The other objective of the present invention is a process for producing an enriched colorless tetrahydrotetrahydroxycurcumin (THTC) from the above said enriched tetrahydroxycurcumin fraction and a method for treating various inflammatory conditions and also for preventing various oxidative disease conditions by administering the inventive colorless tetrahydrotetrahydroxycurcumin fraction.

Yet another object of the present invention is a method for isolating TC, DC, DMDC and BDC in pure form by column chromatography, followed by crystallization.

DETAILED DISCLOUSURE OF THE INVENTION

Organic solvent extracts of the *curcuma* species, particularly *Curcuma longa* have been found to contain a total of four curcumins. These are shown in FIG. 1 and are represented by C, MDC, BDC and TC. Concentration of tetrahydroxycurcumin, designated as TC in the FIG. 1, amounts only in the range of 0.1 to 5% in the natural curcumin fraction (Mimura Akio et al., U.S. Pat. No. 5,266,344, 1993). Among the four curcumins, TC showed most potent anticancer, antioxidant and anti-inflammatory activities. However, there is no report on the enrichment process of TC in curcumin mixture.

The present invention is aimed at enriching the concentration of TC in the curcumin fraction to a desired concentration upto 100%. Another objective of this invention is to convert less potent curcumins present in the extract by demethylating them to highly potent antioxidative demethylcurcumins. The said demethylation leads to a fraction, which contains higher concentration of TC. Pure TC could also be obtained from the TC enriched fraction by a simple purification process.

A combination of simple chemical reaction and purification by chromatographic method achieves these objectives.

FIG.-2: Chemical structures of the components of the enriched fraction of tetrahydroxycurcumin

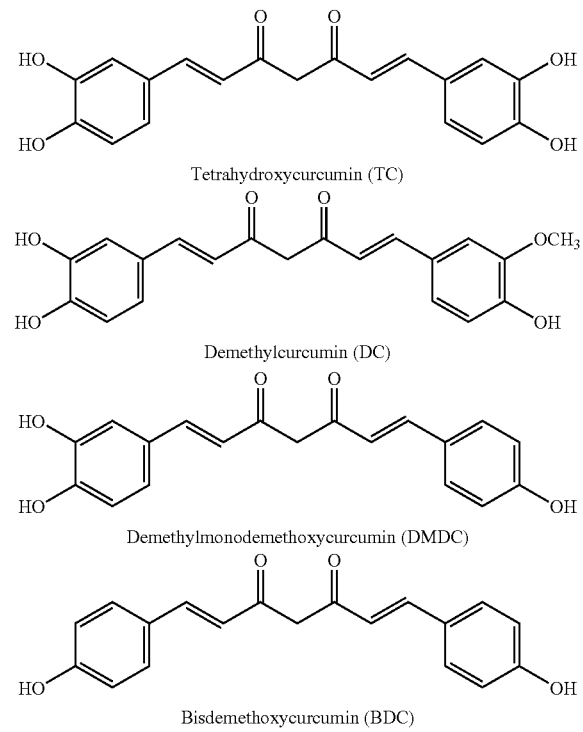

The present inventive enriched tetrahydroxycurcumin fraction obtained from the natural *Curcuma* extract contains a total of four compounds. These are shown in FIG. 2 and are represented by TC, DC, BMDC and BDC. Concentration of TC is in the range of 10-100%.

The process involves demethylation of *Curcuma longa* extracts by Lewis acid catalyst in a suitable solvent to an enriched fraction of tetrahydroxycurcumin. An organic base and a catalyst in addition to aluminum halides are used for demethylation. Dry material obtained after simple work-up showed 50-80% of TC by HPLC analysis.

The Lewis acid catalysts such as aluminum chloride, aluminum bromide, aluminum iodide, broron tribromide or boron trichloride-methyl sulfide complex or sodium salt of N-methylaniline or sodium ethanethiolate or lithium chloride in dimethyl formamide or beryllium chloride are used. Solvents such as chloroform, dichloromethane, dichloroethane and ethyl acetate or mixtures thereof are used. Organic bases such as pyridine, triethylamine, piperidine are used and catalyst is selected from sodium iodide or potassium iodide or PTC catalyst such as tetrabutylammonium bromide etc. are used.

Pure TC is obtained from the enriched tetrahydroxycurcumin fraction by chromatographic methods. Solid supports such as silica gel, reversed phase silica, alumina and sephadex can be used in the process. Chromatographic techniques are selected from gravity column, flash chromatography, reversed phase chromatography, preparative high pressure liquid chromatography and the combinations thereof. Solvents such as acetone, chloroform, dichloromethane, ethyl acetate, hexane and water either alone or in combination to run a gravity column or flash column or medium pressure column are used.

This invention relates to a process for producing 50% to 100% of TC from the extracts of *Curcuma* species particularly *Curcuma longa*, which comprises the steps of demethylation of the said extracts, followed by chromatographic separation to obtain a fraction enriched in TC in the range of 50 to 100%.

The invention also relates to a process for isolating all the four compounds in the present inventive tetrahydroxycurcumin fraction in pure form by column chromatography using polar and non-polar solvents as eluents, followed by crystallizations. The structures of the isolated pure TC, DC, DMDC and BDC (FIG. 2) have been confirmed by their physical and spectral data (IR, NMR and mass).

Though the above enriched tetrahydroxycurcumin fraction exhibits strong antioxidative activity than the curcumins, but its application may be limited because of its strong yellow color. For application in colorless foods and cosmetics, we have invented a colorless tetrahydrotetrahydroxycurcumin fraction by a process of hydrogenation. The process of hydrogenation of curcumins could also occur naturally in the gastrointestinal tract. The tetrahydrotetrahydroxycurcumin fraction is also strong antioxidant similar to tetrahydroxycurcumin combined with the lack of yellow color render them useful in achromatic food and cosmetic applications that currently employ conventional synthetic antioxidants.

So the invention is also aimed to obtain a colorless tetrahydrotetrahydroxycurcumin (THTC) enriched fraction.

FIG.-3: Chemical constituents of the tetrahydrotetrahydroxycurcumin fraction

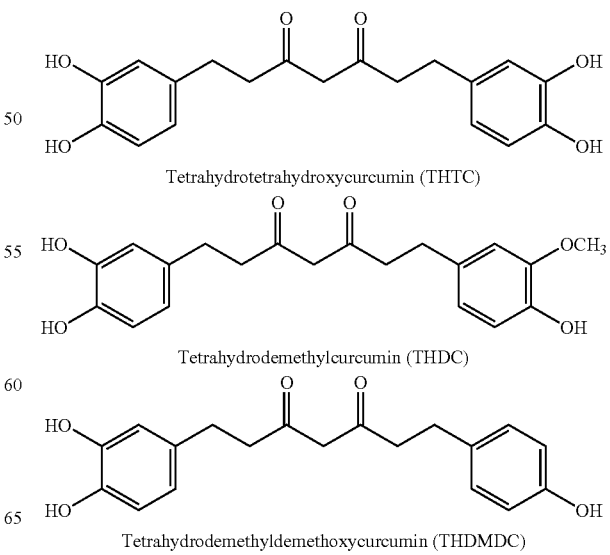

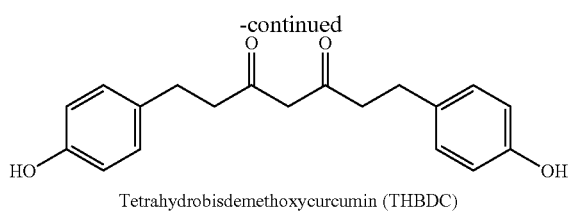
Tetrahydrobisdemethoxycurcumin (THBDC)

The presently invented colorless tetrahydrotetrahydroxycurcumin enriched fraction from the said tetrahydroxycurcumin fraction has been found to contain a total of four tetrahydro compounds. These are shown in FIG. 3 and are represented by tetrahydrotetrahydroxycurcumin (THTC), tetrahydrodemethylcurcumin (THDC), tetrahydrodemethylmonodemethoxycurcumin (THBMDC) and tetrahydrobisdemethoxycurcumin (THBDC). Concentration of THTC is in the range of 10-100%.

The process involves the hydrogenation of TC enriched fraction by reducing the double bonds using metal catalyst in a suitable solvent and a hydrogen gas or hydrogen donor to an enriched fraction of tetrahydrotetrahydroxycurcumin (THTC). An organic base is also used if desired.

The metal catalysts such as palladium-carbon, Raney-nickel, platinum, zinc or manganese are used. Solvents such as ethyl acetate, acetone, methanol, ethanol, isopropanol, tetrahydrofuran, dioxane or mixtures thereof are used. Hydrogen donors such as formic acid, acetic acid, propanoic acid or ammonium formate are used. Organic bases such as triethyl amine, trimethyl amine or piperidine are used.

Pure THTC is obtained from the enriched fraction of tetrahydrotetrahydroxycurcumin by chromatographic methods as described above. Pure THTC could also be obtained by the hydrogenation of pure TC.

The invention also describes a method of treating inflammatory conditions by use of the above said enriched tetrahydroxycurcumin or purified TC or colorless tetrahydotetrahydroxycurcumin and the activity was supported by the measurement of 5-lipoxygenase activity. From the percentage of 5-lipoxygenase inhibitory values (Table 1) of the present inventive tetrahydoxycurcumin fraction or pure TC or tetrahydrotetrahydroxycurcumin showed potent 5-lipoxygenase activity and the activity is superior to that of existing commercial curcumin mixture and comparable to that of AKBA, a potent 5-lipoxygenase inhibitor from *Boswellia serrata*.

The invention also describes a method of treating or preventing radical mediated complications in humans or in foods by the use of above said enriched fraction of tetrahydroxycurcumin or purified TC or colorless tetrahydrotetrahydroxycurcumin and the activity was supported by the measurement of superoxide and DPPH radical scavenging activity. From the percentage of inhibitory values (Table 2) of the present inventive enriched tetrahydroxycurcumin fraction or pure TC or colorless tetrahydrotetrahydroxycurcumin showed potent antioxidative activity and the activity is superior to that of existing commercial curcumin mixture, BHT (butylatedhydroxytoluene), BHA (butylated hydroxyanisole), vitamin C and vitamin E.

The invention also describes use of enriched tetrahydroxycurcumin fraction containing 70-100% of TC for treating anti-inflammatory conditions. The anti-inflammatory activity was demonstrated by the carragenean induced paw edema method. The above enriched TC fraction showed 20.56% inhibition at 50 mg concentration, whereas the standard drug, diclofenac sodium showed 63.10% inhibition at 25 mg concentration. From these results it is clear that the present inventive tetrahydroxycurcumin fraction showed significant anti-inflammatory activity.

A further aspect of the present invention is a pharmaceutical formulation comprising a enriched fraction of tetrahydroxycurcumin fraction or TC or colorless tetrahydrotetrahydroxycurcumin as described above in a pharmaceutically acceptable carrier (e.g., an aqueous or a non aqueous carrier).

A still further aspect of the present invention is a method of treating inflammatory diseases, comprising administering to a human or animal subject in need thereof a therapeutically effective amount (e.g., an amount effective to treat, slow the progression of, etc.) of a enriched tetrahydroxycurcumin fraction or pure TC or colorless tetrahydrotetrahydroxycurcumin as described above.

A still further aspect of the present invention is a method of preventing radical mediated diseases, comprising administering to a human or animal subject in need thereof a therapeutically effective amount (e.g., an amount effective to treat, slow the progression of, etc.) of a enriched tetrahydroxycurcumin or pure TC or colorless tetrahydrotetrahydroxycurcumin as described above.

The invention is described in the examples given below which are provided by a way of illustrations only and should not be construed to limit the scope of the present invention.

EXAMPLE 1

Enriched fraction of tetrahydroxycurcumin To an ice cold solution of curcumin mixture (95%, 55 g) in EtOAc (2.5 L), was added aluminum chloride (150 g) followed by the dropwise addition of pyridine (350 mL) for 15 min. and the reaction mixture was heated under reflux for 7 h. After cooling the reaction mixture to 10° C., cold dil. HCl (20%) was added to decompose aluminum chloride complex and extracted with ethyl acetate (5×1.0 L). The combined ethyl acetate layer was washed with water, brine and dried over anhydrous sodium sulfate. The solvent was filtered and evaporated the solvent. The residue was diluted with chloroform (100 mL) and kept for 10 h and the solid was filtered and dried to give the product (21 g, 38%).

HPLC analysis:

| TC = | 78.40 |
|---|---|
| DC = | 4.11 |
| DMDC = | 11.52 |
| BDC = | 0.86 |
| Total = | 94.89% |

EXAMPLE 2

Enriched fraction of tetrahydroxycurcumin. To an ice cold solution of curcumin mixture (95%, 110 g) in EDC (4 L), was added dry aluminum chloride (160 g) followed by the dropwise addition of pyridine (distilled, 200 mL) for 15 min. followed by sodium iodide (5 g) and the reaction mixture was heated under reflux for 27 h. After cooling the reaction mixture to 10° C., diluted with water (2 L), acidified with HCl (50%) and stirred for 15 min. The organic layer was separated and water was added to the aqueous layer until 10 L volume. The aqueous layer was stirred at rt for 2 h and settled for 16 h. The solids formed were filtered and washed with water (2.5 L) and dried to give the crude mixture of demethylcurcumins, 94 g, which was stirred in ethyl acetate (2.5 L) at 70-80° C. for 1 h, filtered through supercel and evaporated the solvent to give the product, 84 g. This solid was stirred with diethyl ether (500 mL) at rt for 30 min. and filtered, dried to give the product 58 g.

HPLC analysis:

| | |
|---|---|
| TC = | 75.68 |
| DC = | 6.32 |
| DMDC = | 11.24 |
| BDC = | 1.1 |
| Total = | 95.31% |

EXAMPLE 3

Isolation of pure TC [1,7-Bis(3,4-dihydroxyphenyl)-1,6-heptadiene-3,5-dione]. The demethylcurcumin mixture (1 Kg, 75% TC) from example 2, was adsorbed over silica gel (100-200 mesh, 2 Kg) and chromatographed over silica gel column using chloroform-methanol (95:5) as eluents to give pure TC, which was crystallized from chloroform-methanol as yellow color powder (0.5 Kg), mp 302-304° C.; IR (KBr): 3488, 3386, 1629, 1617, 1600, 1271, 1289, 1142, 1120, 955 cm$^{-1}$; $^1$H NMR (DMSO-d$_6$) δ 6.06 (1H, s, H-4), 6.56 (2H, d, J=15.6 Hz, H-2,6), 6.77 (2H, d, J=8.3 Hz, H-5',5"), 7.00 (2H, d, J=1.8 Hz, H-2',2"), 7.06 (2H, dd, J=8.3, 1.8 Hz, H-6',6"), 7.44 (2H, d, J=15.6 Hz, H-1,7), $^{13}$C NMR (DMSO-d$_6$) δ 183.1, 147.8, 145.1, 140.8, 127.7, 126.5, 121.9, 115.9, 114.5, 100.9; LC-MS m/z (%): (ESI-negative mode) 339 [(M−H)$^-$, 100].

EXAMPLE 4

Isolation and characterisation of other ingradients in tetrahydroxycnrcumin fraction. The demethylcurcumin mixture (1 Kg) from example 2, was adsorbed over silica gel (100-200 mesh, 2 Kg) and chromatographed over silica gel column using chloroform-methanol (95:5) as eluents to give pure DC, DMDC and BDC. The following are the spectral data of the isolated compounds.

DC [1-(3,4-dihydroxyphenyl)-7-(3-methoxy-4-hydroxyphenyl)-1,6-heptadiene-3,5-dione]. Yellow color powder, mp 164-166° C.; IR (KBr): 3484, 1621, 1267, 1132, 1140, 964 cm$^-$, $^1$H NMR. (DMSO-d$_6$) δ 3.82 (3H, s, Ar—OCH$_3$), 6.04 (1H, s, H-4), 6.53 (1H, d, J=16.0 Hz, 11-2 or H-6), 6.74 (1H, d, J=16.0 Hz, 11-2 or H-6), 6.76 (1H, d, J=8.5 Hz, H-5'), 6.80 (1H, d, J=8.3 Hz, H-5"), 7.07 (1H, dd, J=8.5, 1.8 Hz, H-6'), 7.00 (1H, d, J=1.8 Hz, H-2'), 7.12 (1H, d, J=1.8 Hz, H-2"), 7.29 (1H, dd, J=8.3, 1.8 Hz, H-6"), 7.44 (1H, d, J=16.0 Hz, H-1 or H-7), 7.51 (1H, d, J=16.0 Hz, H-1 or H-7); $^{13}$C NMR (DMSO-d$_6$): 183.0, 183.2, 148.6, 147.9, 147.7, 145.1, 140.8, 140.7, 126.5, 122.8, 121.9, 121.0, 120.7, 115.9, 115.6, 114.6, 111.0, 101.0, 55.4; EIMS m/z (%): 354 (M$^+$, 16), 336 (20), 328 (54), 271 (71), 192 (53), 191 (30), 177 (100), 167 (47), 163 (49), 150 (40), 149 (24), 145 (84), 135 (48), 117 (42), 89 (57), 77 (43).

DMDC [1-(4-hydroxyphenyl)-7-(3,4-dihydroxyphenyl)-1,6-heptadiene-3,5-dione]. Yellow color powder, mp 218-220° C.; IR. (KBr): 3338, 1627, 962 cm$^{-1}$; $^1$H NMR (DMSO-d$_6$) δ 6.06 (1H, s, H-4), 6.59 (1H, d, J=15.8 Hz, H-2 or H-6), 6.69 (1H, d, J=15.8 Hz, H-2 or H-6), 6.83 (1H, d, J=8.2 Hz, H-5"), 6.79 (2H, d, J=8.0 Hz, H-3',5'), 7.03 (1H, s, H-2"), 7.09 (1H, d, J=8.2 Hz, H-6"), 7.45 (1H, d, J=15.9 Hz, H-1 or H-7), 7.47 (1H, d, J=15.9 Hz, H-1 or H-7), 7.57 (2H, d, J=8.0 Hz, H-2',6'), 9.17 (1H, br s, Ar—OH), 9.63 (1H, br s, Ar—OH), 10.04 (1H, br s, Ar—OH); EIMS m/z (%): 324 (M$^+$, 18), 306 (8), 299 (34), 298 (90), 242 (30), 241 (100), 163 (49), 161 (26), 162 (38), 147 (87), 110 (43), 119 (39), 91 (21), 44 (34).

BDC [1,7-bis(4-hydroxyphenyl)-1,6-heptadiene-3,5-dione]. Yellow color powder, mp 222-224° C.; IR (KBr): 3211, 1620, 1600, 1269, 1168, 1140, 955, 831 cm$^{-1}$; $^1$H NMR (DMSO-d$_6$) δ 6.03 (1H, s, H-4), 6.68 (2H, d, J=16.0 Hz, H-2,6), 6.80 (4H, d, J=8.0 Hz, H-3',5',3",5"), 7.50 (2H, d, J=16.0 Hz, H-1,7), 7.55 (4H, d, J=8.0 Hz, H-2',6',2",6"); EIMS m/z (%): 308 (M$^+$, 20), 290 (14), 159 (36), 146 (100), 147 (87), 119 (38), 106 (42), 90 (42), 65 (32).

EXAMPLE 5

Enriched fraction of tetrahydrotetrahydroxycurcumin. To a solution of enriched fraction of tetrahydroxycurcurnin (95%, 25 g) from example 2, in ethyl acetate (100 mL) was added triethyl amine (50 mL) and palladium-calcium carbonate (5%, 3.75 g) followed by dropwise addition of formic acid (8 mL) for 1 h at refluxing temperature. The reaction mixture was refluxed for 8 h. Formic acid (4.5 mL) was added periodically at 2 h intervals. After completion of the reaction, solvents were distilled off (appr. 50 mL). The cooled reaction mixture was acidified with HCl (50%) and diluted with ethyl acetate (100 mL). The solution was filtered through supercel and separated the ethyl acetate layer. The aqueous layer was further extracted with ethyl acetate (2×100 mL) and the combined ethyl acetate layer was washed with water, brine and dried over sodium sulfate. The solution was filtered and evaporated upto 10 mL volume and diluted with hexane (20 mL). The solution was passed through silica gel column using chloroform-methanol (10%, 100 mL) as eluents to give the product (13 g) as a low melting solid.

HPLC Analysis:

| | |
|---|---|
| THTC = | 72.86% |
| THDC = | 15.98% |
| THDMDC = | 7.56% |
| THBDC = | 0.12% |
| Total = | 96.39% |

Antioxidant Activity (a) Superoxide free radical scavenging activity. The superoxide free radical scavenging activity was determined by the NBT (nitro blue tetrazolium) method. The reaction mixture contained EDTA (6.6 mM), NaCN (3 pg), riboflavin (2 NBT (50 μM), various concentrations of the test drug in ethanol and a phosphate buffer (58 mM, pH 7.8) in a final volume of 3 ml. Optical density was measured at 560 nm. The test tubes were uniformly illuminated with an incandescent lamp for 15 min, after which the optical density was measured again at 560 nm. The percentage inhibition and superoxide radical generation was measured by comparing the absorbance values of the control and those of the test compounds. IC$_{50}$ values were obtained from plot of the concentration in μg against the percentage inhibition.

(b) DPPH free radical scavenging activity. DPPH (1,1-diphenyl-2-picryl-hydrazyl) radical scavenging activity was measured based on the reduction of methanolic solution of the colored DPPH. Free radical scavenging ability of the test drug in ethanol added to the methanolic solution of DPPH is inversely proportional to the difference in initial and final absorption of DPPH solution at 516 nm. The reaction mixture contained 1×10$^{-4}$ mM methanolic solution of DPPH and various concentrations of test drugs. The percentage inhibition was determined by comparing the absorbance values of test and control tubes.

5-Lipoxygenase activity: The enriched fraction of tetrahydroxycurcumin mixture, pure TC and tetrahydrotetrahydroxycurcumin fraction were screened for their 5-Lipoxygenase inhibitory potential using colorimetric method. The assay mixture contained 50 mM phosphate buffer pH 6.3, 5-Lipoxygenase, various concentrations of test substances in dimethyl sulphoxide and linoleic acid in a total volume of 0.5 mL, after 5 min incubation of above reaction mixture, 0.5 mL ferric xylenol orange reagent was added and OD was measured after two minutes at 585 nm using spectrophotometer. Controls were run along with test in a similar manner except using vehicle instead of test substance solution. Percent inhibition was calculated by comparing absorbance of test solution with that of control.

Anti-inflammatory activity (Carragenin induced paw edema method): Prior to the experiment all the animals (Albino wistar rats of either sex weighing between 180-300 g) fasted at ad libitum water and were weighed, numbered and randomly divided into groups, each containing 3 animals. Initial paw volumes were measured using plethesmometer and noted. All the groups were treated with corresponding test substance orally using gastric tube. Control group was treated with 10 mL/Kg vehicle (0.5%, carboxymethyl cellulose sodium salt). After 30 minutes, all the animals were injected subcutaneously at subplantar region of left hind paw 1% carrageenin 0.1 mL using hypodermic needle. All the animals were administered water 20 mL/Kg body weight and kept devoid of water for 3 h (maintained uniform hydration). After 3 h, paw volumes of all the animals were measured twice and average volume from two measurements were recorded. The % of inhibition of paw edema was calculated by comparing paw edema of test substance treated groups with that of control groups.

TABLE 1

Antioxidant activity

| S. No. | Name of the compound | Superoxide (NBT) $IC_{50}$ in μg | DPPH $IC_{50}$ in μg |
|---|---|---|---|
| 1 | Natural curcumins mixture (95%) | 27.5 | 2.9 |
| 2 | Enriched tetrahydroxycurcumin fraction (95%) | 3.1 | 1.1 |
| 3 | Pure tetrahydroxycurcumin (TC) | 2.5 | 1.1 |
| 4 | Tetrahydrocurcumins mixture | >100 | 2.9 |
| 5 | Enriched Tetrahydrotetrahydroxycurcumin fraction | 3.0 | 1.5 |
| 6 | Pure tetrahydrotetrahydroxycurcumin (THTC) | 4.0 | 1.6 |
| 7 | BHT | 90 | 5.3 |
| 8 | BHA | 174 | 6.1 |
| 9 | Vitamin C | 150 | 4.4 |

BHA: Butylated hydroxyanisole; BHT: Butylated hydroxytoluene

TABLE 1-continued

Antioxidant activity

| S. No. | Name of the compound | Superoxide (NBT) $IC_{50}$ in μg | DPPH $IC_{50}$ in μg |
|---|---|---|---|

The lower the $IC_{50}$ value, the higher is the antioxidant activity.

TABLE 2

5-Lipoxygenase inhibitory activity

| S. No. | Name of the compound | Concentration in μg/mL | % of inhibition |
|---|---|---|---|
| 1 | Natural curcumins mixture (95%) | 160 | 22 |
| 2 | Enriched tetrahydoxycurcumin fraction (95%) | 4 | 51 |
| 3 | Pure tetrahydroxycurcumin (TC) | 16 | 60 |
| 4 | Tetrahydrocurcumins mixture | 100 | Nil |
| 5 | Enriched tetrahydrotetrahydroxycurcumin fraction | 50 | 46 |
| 6 | Pure tetrahydrotetrahydroxycurcumin (THTC) | 80 | 0.2 |
| 7 | AKBA | 41 | 55 |
| 8 | NDGA | 24 | 60 |

AKBA: Acetyl-keto-boswellic acid; NDGA: Nordihydroguaiaretic acid

The invention claimed is:

1. A composition comprising tetrahydrotetrahydroxycurcumin in the range of 30-80%; tetrahydrodemethylcurcumin in the range of 4-20%; tetrahydrodemethylmonodemethoxycurcumin in the range of 5-25% and tetrahydrobisdemethoxycurcumin in the range of 0.1-10%.

2. A pharmaceutical or dietary supplement with anti-oxidative and anti-inflammatory activity comprising a therapeutically effective amount of the composition of claim 1, wherein said pharmaceutical or dietary supplement further comprises one or more pharmaceutically acceptable excipients.

3. A composition comprising tetrahydroxycurcumin in the range of 30-80%; demethylcurcumin in the range of 4-20%; demethylmonodemethoxy curcumin in the range of 5-25%; and bisdemethoxycurcumin in the range of 0.1-10%.

4. A pharmaceutical or dietary supplement with anti-oxidative and anti-inflammatory activity comprising a therapeutically effective amount of the composition of claim 3, wherein said pharmaceutical or dietary supplement further comprises one or more pharmaceutically acceptable excipients.

5. A method for treating inflammation comprising administering to a mammal in need thereof, a therapeutically effective amount of the composition of claim 1.

6. The method of claim 5 wherein said mammal is a human.

7. A method for treating inflammation comprising administering to a mammal in need thereof, a therapeutically effective amount of the composition of claim 3.

8. The method of claim 7 wherein said mammal is a human.

* * * * *